(12) United States Patent
Freed et al.

(10) Patent No.: US 9,733,383 B2
(45) Date of Patent: Aug. 15, 2017

(54) METHODS FOR COMPOSITIONAL ANALYSIS OF DOWNHOLE FLUIDS USING DATA FROM NMR AND OTHER TOOLS

(71) Applicant: SCHLUMBERGER TECHNOLOGY CORPORATION, Sugar Land, TX (US)

(72) Inventors: Denise E. Freed, Newton Highlands, MA (US); Lalitha Venkataramanan, Lexington, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 765 days.

(21) Appl. No.: 14/109,497

(22) Filed: Dec. 17, 2013

(65) Prior Publication Data

US 2015/0168587 A1    Jun. 18, 2015

(51) Int. Cl.
*G01V 3/32* (2006.01)
*E21B 49/08* (2006.01)
*G01N 24/08* (2006.01)
*G01V 11/00* (2006.01)

(52) U.S. Cl.
CPC .............. *G01V 3/32* (2013.01); *E21B 49/088* (2013.01); *G01N 24/081* (2013.01); *G01V 11/00* (2013.01)

(58) Field of Classification Search
CPC ........ G01V 3/32; G01V 11/00; E21B 49/088; G01N 24/081
See application file for complete search history.

(56) References Cited

U.S. PATENT DOCUMENTS

| | | | |
|---|---|---|---|
| 6,859,032 B2 | 2/2005 | Heaton et al. | |
| 7,253,617 B1 | 8/2007 | Chen et al. | |
| 2004/0253743 A1 | 12/2004 | Freed | |
| 2005/0242807 A1* | 11/2005 | Freedman | G01V 11/00 324/303 |
| 2008/0154509 A1 | 6/2008 | Heaton | |
| 2009/0289628 A1 | 11/2009 | Cao Minh | |
| 2010/0236326 A1 | 9/2010 | Freed et al. | |

(Continued)

FOREIGN PATENT DOCUMENTS

| | | |
|---|---|---|
| EP | 1003053 A2 | 5/2000 |
| WO | 2008048357 A2 | 4/2008 |
| WO | 2013066953 A2 | 5/2013 |

OTHER PUBLICATIONS

Anand, et al., "New Method for Predicting Properties of Live Oils from NMR", Petrophysics, vol. 53, No. 4, 2012, pp. 256-271.

(Continued)

*Primary Examiner* — Gregory H Curran

(57) ABSTRACT

Methods and apparatuses are provided for analyzing a composition of a hydrocarbon-containing fluid. The methods include using a nuclear magnetic resonance (NMR) tool to conduct NMR measurements on the hydrocarbon-containing fluid to obtain NMR data. A non-NMR tool, such as an optical tool, is used to conduct additional measurements and to obtain non-NMR data on the fluid. The methods further include determining an indication of the composition of the fluid by using the NMR data and normalizing the indication of the composition of the fluid using the non-NMR data.

20 Claims, 3 Drawing Sheets

(56) References Cited

U.S. PATENT DOCUMENTS

| | | |
|---|---|---|
| 2011/0175607 A1* | 7/2011 | Fordham .............. E21B 43/16 324/303 |
| 2013/0113480 A1 | 5/2013 | Kadayam Viswanathan et al. |
| 2015/0168585 A1 | 6/2015 | Bennet et al. |
| 2015/0168586 A1 | 6/2015 | Freed et al. |

OTHER PUBLICATIONS

Anand, et al., "New Methods for Predicting Properties of Live Oils From Nmr", SPWLA 50th Annual Logging Symposium, The Woodlands, Texas, Jun. 21-24, 2009, 15 pages.
Badry, et al., "Downhole Optical Analysis of Formation Fluids", Oilfield Review, vol. 6, Issue 1, Jan. 1994, pp. 21-28.
Cavalleri, et al., "Wireline Logging Including 2-Dimensional NMR and Downhole Spectroscopy Facilitates Accurate Identification of Pay and Composition of Formation Fluids in a Complex Reservoir", OMC-2013-178, Offshore Mediterranean Conference and Exhibition, Ravenna, Italy, Mar. 20-22, 2013, 9 pages.
Donaldson, et al., "Mean carbon number logging: hydrocarbon chain length determination using diffusion distributions at multiple depths", SPWLA 54th Annual Logging Symposium, Jun. 22, 2013, pp. 1-8.
Epstein, et al., "The Bad Truth about Laplace's Transform", SIAM Rev., vol. 50, No. 3, 2008, pp. 504-520.
Fordham, et al., "Imaging Multiexponential Relaxation in the (Y1 Loge T1) Plane, with Application to Clay Filtration in Rock Cores", Journal of Magnetic Resonance Series A, vol. 113, No. 2, Apr. 1995, pp. 139-150.
Freed, "Dependence on chain length of NMR relaxation times in mixtures of alkanes", Journal of Chemical Physics, vol. 126, No. 17, 2007, 10 pages.
Freed, et al., "One- and two-dimensional spin correlation of complex fluids and the relation to fluid composition", Comptes Rendus Physique, vol. 11, Issue 2, Mar. 2010, pp. 181-191.
Freed, et al., "Scaling Laws for Diffusion Coefficients in Mixtures of Alkanes", Physical Review Letters, vol. 9, No. 6, Feb. 17, 2005, 4 pages.
Morriss, et al., "Hydrocarbon Saturation and Viscosity Estimation From Nmr Logging in the Belridge Diatomite", The Log Analyst, vol. 38, Issue 2, 1997, pp. 44-59.
Fujisawa, et al., "Analyzing Reservoir Fluid Composition In-Situ in Real Time: Case Study in a Carbonate Reservoir", SPE 84092—SPE Annual Technical Conference and Exhibition, Denver, Colorado, Oct. 2003, pp. 1-9.
Fujisawa, et al., "Live Oil Sample Acquisition and Downhole Fluid Analysis", Asphaltenes, Heavy Oils, and Petroleomics, Chapter 22, Springer, New York, 2007, pp. 589-616.
Fujisawa, et al., "Near-Infrared Compositional Analysis of Gas and Condensate Reservoir Fluids at Elevated Pressures and Temperatures", Applied Spectroscopy, vol. 56, No. 12, 2002, pp. 1615-1620.
Godefroy, et al., "Discussion on Formation Fluid Density Measurements and Their Applications", SPE 114648—SPE Annual Technical Conference and Exhibition, Denver, Colorado, Sep. 21-24, 2008, 20 pages.

Hurlimann, et al., "Hydrocarbon Composition From NMR Diffusion and Relaxation Data", Petrophysics, vol. 50, No. 2, 2009, pp. 116-129.
Jestin, et al., "Application of NMR Solvent Relaxation and SAXS to Asphaltenes Solutions Characterization", Journal of Dispersion Science and Technology, vol. 25, No. 3, Jan. 2004, pp. 341-347.
Kleinberg, "NMR properties of reservoir fluids", The Log Analyst, vol. 37, No. 6, 1996, pp. 20-32.
Lo, et al., "Correlations of NMR Relaxation Time with Viscosity, Diffusivity, and Gas/Oil Ratios of Methane/Hydrocarbon Mixtures", SPE 63217—SPE Annual Technical Conference and Exhibition, Dallas, Texas, Oct. 1-4, 2000, 15 pages.
Mullins, et al., "Hydrocarbon Compositional Analysis In-Situ in Openhole Wireline Logging", SPWLA 45th Annual Logging Symposium, Jun. 6-9, 2004, pp. 1-14.
Mullins, et al., "The colloidal structure of crude oil and the structure of oil reservoirs", Energy & Fuels, vol. 21, 2007, pp. 2785-2794.
Mutina, et al., "Correlation of Transverse and Rotational Diffusion Coefficient: A Probe of Chemical Composition in Hydrocarbon Oils", Journal of Physical Chemistry A, vol. 112, No. 15, 2008, pp. 3291-3301.
Straley, "Reassessment of Correlations Between Viscosity and NMR Measurements", SPWLA 47th Annual Logging Symposium, Veracruz, Mexico, Jun. 4-7, 2006, 14 pages.
Van Steene, et al., "Fluid identification in light hydrocarbons using NMR and downhole fluid analysers", SPE North Africa Technical Conference and Exhibition, Feb. 14-17, 2012, pp. 1-13.
Venkataramanan, et al., "Applications of Mellin Transform in NMR", Journal of Modeling, Design, and Simulation, vol. 1, Jun. 2010, pp. 46-54.
Venkataramanan, et al., "Mellin transform of CPMG data", Journal of Magnetic Resonance, vol. 206, No. 1, Sep. 2010, pp. 20-31.
Venkataramanan, et al., "Solving Fredholm Integrals of the First Kind With Tensor Product Structure in 2 and 2.5 Dimensions", IEEE Transactions on Signal Processing, vol. 5, No. 5, May 2002, pp. 1017-1026.
Zhang, et al., "Oil and Gas NMR Properties: The Light and Heavy Ends", SPWLA 43rd Annual Logging Symposium, Oiso, Japan, Jun. 2-5, 2000, 13 pages.
Zielinski, et al., "Probing Asphaltene Aggregation in Native Crude Oils with Low-Field NMR", Langmuir, vol. 26, No. 7, 2010, pp. 5014-5021.
Kleinberg, "Well Logging", Encyclopedia of NMR, Wiley, New York, 1996, 12 pages.
International Search Report and Written Opinion issued in related PCT application PCT/US2014/066859 on Mar. 23, 2015, 11 pages.
International Search Report and Written Opinion issued in related PCT application PCT/US2014/066845 on Mar. 23, 2015, 10 pages.
International Search Report and Written Opinion issued in related PCT application PCT/US2014/062917 on Feb. 11, 2015, 15 pages.
Hurlimann, et al., "Hydrocarbon Composition From NMR Diffusion and Relaxation Data", SPWLA 49th Annual Logging Symposium, Edinburgh, Scotland, May 25-28, 2008, 14 pages.

* cited by examiner

US 9,733,383 B2

METHODS FOR COMPOSITIONAL ANALYSIS OF DOWNHOLE FLUIDS USING DATA FROM NMR AND OTHER TOOLS

CROSS REFERENCE TO RELATED APPLICATIONS

This Application is related to U.S. patent application Ser. No. 14/109,447 and 14/109,354, both entitled "Methods for Compositional Analysis of Downhole Fluids Using Data from NMR and Other Tools" and filed on Dec. 17, 2013, which are hereby incorporated by reference in their entirety herein.

FIELD

The subject disclosure generally relates to hydrocarbon-bearing geological formations. More particularly, the subject disclosure relates to methods for analyzing the compositional analysis of downhole fluids using nuclear magnetic resonance (NMR) and other data from downhole tools.

BACKGROUND

Optical (spectral) data from downhole fluid analysis logging tools are currently being used to determine the composition of crude oils downhole. See, e.g., Fujisawa, G., et al., "Near-infrared Compositional Analysis of Gas and Condensate Reservoir Fluids at Elevated Pressures and Temperatures," *Applied Spectroscopy*, 52(12: 1615-1620 (2002); Fujisawa, G. et al., "Analyzing Reservoir Fluid Composition In-Situ in Real Time: Case Study in a Carbonate Reservoir", *SPE* 84092, Annual Technical Conference and Exhibition, Denver, Colo. (2002) which are both hereby incorporated by reference herein in their entireties. These determinations are restricted to a subset of components or pseudocomponents including $C_1$ (methane) to $C_5$ (pentane), such as $C_1$, $C_2$-$C_5$, and also $C_{6+}$. The optical tools measure the optical densities $\{OD\}$ at a set of wavelengths $\lambda_i$. These are then used to determine the weight percent $w_{cj}$ of components and pseudo-components such as $C_1$, $C_2$-$C_5$ and $C_{6+}$, or $C_1$, $C_2$, $C_3$-$C_5$ and $C_{6+}$. The individual weight percents for $C_2$, $C_3$, $C_4$, and $C_5$ can then be further resolved using a delumping algorithm. For some of the optical tools, the amount of water and carbon-dioxide ($CO_2$) can also be determined. In addition, the optical density can be used to obtain information about asphaltenes and resins. See, e.g., Mullins, O. C., et al., "The Colloidal Structure of Crude Oils and the Structure of Reservoirs," *Energy Fuels*, 21:2785-2794 (2007) which is hereby incorporated by reference herein in its entirety.

NMR relaxation and diffusion data can also be used to determine oil composition. From this data, the average chain length and the chain length distribution can be obtained. See, e.g., Freed, D. E., et al., "Scaling Laws for Diffusion Coefficients in Mixtures of Alkanes," *Phys. Rev. Lett.*, 94:067602 (2005); Freed, D. E., "Dependence on Chain Length of NMR Relaxation Times in Mixtures of Alkanes," *J. Chem. Phys.*, 126:174502 (2007); Hurlimann, M. D. et al., "Hydrocarbon Composition from NMR Diffusion and Relaxation Data," *SPWLA*, 49th Annual Logging Symposium (May 2008); U.S. Pat. No. 6,859,032 to Heaton, N.J., and Freedman, R.; Anand, V. and Freedman, R., "New Methods for Predicting Properties of Live Oils from NMR," *SPWLA*, Paper AAAA Proceedings of the 2009 Annual SPWLA Symposium (2009), which are all incorporated by reference herein in their entireties. In addition the comparison of transverse and longitudinal relaxation times and/or diffusion can give some information about asphaltenes, and the shapes of the distributions can be a signal of highly biodegraded oils. See, e.g., Mutina, A. R., and Hurlimann, M. D., "Correlation of Transverse and Rotational Diffusion Coefficient: A Probe of Chemical Composition in Hydrocarbon Oils," *J. Phys. Chem.*, A 112:3291-3301 (2008); Freed, D. E., and Hurlimann, M. D., "One- and Two-Dimensional Spin Correlation of Complex Fluids and the Relation to Fluid Composition," *C. R. Phys.*, 11:181-191 (2010), which are both hereby incorporated by reference herein in their entireties. Furthermore, the measurement of the NMR relaxation dispersion, i.e., the relaxation profile as a function of the applied magnetic field, can yield additional information about the aggregation propensity of the asphaltenes and resins in the crude oil.

NMR relaxation and diffusion measurements can be made with a downhole fluid analysis logging tool. See, Kleinberg, R. L., "Well logging", *Encyclopedia of Nuclear Magnetic Resonance*, John Wiley (1996), which is hereby incorporated by reference herein in its entirety. The NMR tools measure the magnetization $M_i$ at a series of echo times $t_i$. They can also measure the magnetization as a function of wait times $\tau_i$ or as a function of $b_i$, which is a diffusion weighting parameter determined by gradients and time variables. The tool data, such as $\{M_i, t_i\}$, $\{M_i, \tau_i\}$, or $\{M_i, b_i\}$ are used to determine the transverse or longitudinal relaxation time distributions or the diffusion distributions, given by $\{f_j, T_{2j}\}$, $\{f_j, T_{1j}\}$, or $\{f_j, D_j\}$, respectively. For these distributions, $f_j$ is the fraction of protons with relaxation time $T_{2j}$ or $T_{1j}$ or with diffusion coefficient $D_j$, weighted by the total magnetization, $M_0$. These distributions can be related to the raw data by an inversion process, such as an inverse Laplace transform. See, Fordham, E. J. et al., "Imaging multiexponential relaxation in the (y, $\log_d T_1$) plane, with application to clay filtration rock cores," *J. Magn, Reson, A*, 113:139-150 (1995); Venkataramanan, L. et al., "Solving fredholm integrals of the first kind with tensor product structure in 2 and 2.5 dimensions," *IEEE Trans. Signal Process*, 50:1017-1026 (2002), which are both hereby incorporated by reference herein in their entireties. However, this inverse Laplace transform can be problematic because when noise is present, the inversion is non-unique. As a result, a regulator is often introduced to ensure the smoothness of the calculated distributions. These issues introduce some uncertainty into the calculated relaxation and diffusion distributions. See, Epstein, C. L., and Schotland, J., "The bad truth about Laplace's transform," *SIAM Rev.*, 50:504-520 (2008), which is hereby incorporated by reference herein in its entirety.

To obtain the relaxation or diffusion distribution from the raw data, the quantity $\|d-Kf\|^2$ is minimized with the constraint that $f_j$, the components of the vector f, are non-negative. In this expression, d is the vector with components $d_i = M_i$, and $\kappa$ is the kernel. For standard measurements, it is given by $K_{ij} = \exp(t_i/T_{2j})$, $1 - 2\exp(-t_i/T_{1j})$ and $\exp(-b_i D_j)$ for the transverse relaxation, longitudinal relaxation and diffusion, respectively. In the past, the above expression is minimized using methods such as a non-negative least square fit with Tikhonov regularization or by maximum entropy methods.

Once the relaxation or diffusion distributions are known, the NMR data can be used to obtain information about chain length distributions and the viscosity of the oil. The viscosity η of the oil is related to the −1st moment of the diffusion coefficient. See, Freed, D. E., et al., "Scaling laws for diffusion coefficients in mixtures of alkanes," *Phys Rev Lett*. 94:067602 (2005) and Hurlimann, M. D. et al., "Hydrocarbon composition from NMR diffusion and relaxation data," *SPLWA, 49th Annual Logging Symposium* (May 2008). In terms of the log distribution, $f_D$ (log $D_i$), the viscosity is given by $$\eta = CT \frac{\int f_D(\log D_i)/D_i d\log(D_i)}{\int f_D(\log D_i) d\log(D_i)}, \tag{1}$$

where the temperature T is in degrees Kelvin and C has been found to be $3.2\times10^{-8}$cpcn$^2$sK, but can vary somewhat depending on the type of oil. For numerical calculations, the integrals in Eq. (1) are replaced with summations. There are also correlations between viscosity and the mean log diffusion coefficient or relaxation time which appear in the literature. See, e.g., Morriss, C. E., et al., "Hydrocarbon saturation and viscosity estimation from NMR logging in the Beldridge diatomite," *The Log Analyst*, 382:44-59 (1996); Kleinberg, R. L., and Vinegar, H. J., "NMR properties or reservoir fluids," *The Log Analyst*, 376:20-32 (1996); Lo, S., et al., "Correlations of NMR relaxation time with viscosity, diffusivity, and gasoil ratio of methanehydrocarbon mixtures," *Proceedings of the 2000 Annual Technical Conference and Exhibition, Society of Petroleum Engineers* (October, 2000); Straley, C., "Reassessment of correlations between viscosity and NMR measurements," *SPWLA, 47th Annual Logging Symposium* (June 2006) which are all hereby incorporated by reference herein in their entireties.

Several methods have been proposed to relate NMR relaxation and diffusion to chain length distributions. One method makes use of radial basis functions to interpolate between known data and new measurements. See, Anand, V., and Freedman, R., "New methods for predicting properties of live oils from NMR," *Paper AAAA Proceedings of the 2009 Annual SPWLA Symposium* (2009). Another method uses the constituent viscosity model to relate the diffusion coefficients and relaxation times of each component to its microscopic, or constituent, viscosity. See, previously incorporated U.S. Pat. No. 6,859,032. A third method as discussed below is based on looking at mixtures of alkanes, but can apply to oils with other components also.

For the method based on looking at mixtures of alkanes, the average chain length or carbon number (the terms "chain length" and "carbon number" being used interchangeably herein) is defined as $\bar{N}=\Sigma x_j N_j$, where $x_j$ is the mole percent of molecules with chain length $N_j$. For oils high in saturates, this average chain length is related to the $1/v^{th}$ moment of the diffusion distribution and, in the absence of asphaltene, to the $1/\kappa^{th}$ moment of the relaxation time distribution, where $v=0.7$, and $\kappa=1.24$. They are given by Freed, D. E., et al., "Scaling laws for diffusion coefficients in mixtures of alkanes," *Phys Rev Lett.* 94:067602 (2005), and Freed, D. E., "Dependence on chain length of NMR relaxation times in mixtures of alkanes," *J. Chem, Phys.*, 126:174502 (2007):

$$\bar{N} = A^{\frac{1}{\beta+\nu}}\langle D^{1/\nu}\rangle^{\frac{-\nu}{\beta+\nu}}, \text{ and} \tag{2}$$

$$\bar{N} = B^{\frac{1}{\gamma+\kappa}}\langle T_{1,2}^{1/\kappa}\rangle^{\frac{-\kappa}{\gamma+\kappa}}. \tag{3}$$

In these equations, A and B are constants that depend on temperature and pressure, and $\beta$ and $\gamma$ are constants that depend on temperature. The chain length $N_i$ that corresponds to the diffusion coefficient $D_i$ is then given by previously incorporated Freed, D. E., et al., "Scaling laws for diffusion coefficients in mixtures of alkanes," *Phys Rev Lett.* 94:067602 (2005), $$N_i = A^{1/\nu}\bar{N}^{-\beta/\nu}D_i^{-1/\nu} \tag{4}$$

For chain lengths less than about five, this expression should be modified, because, in that case, the molecules act more like hard spheres than chains. Similarly, in the absence of asphaltenes, the chain length that corresponds to the relaxation time is given$_{2i}$ by previously incorporated Freed, D. E., "Dependence on chain length of NMR relaxation times in mixtures of alkanes," *J. Chem, Phys.*, 126:174502 (2007), $$N_i = B^{1/\kappa}\bar{N}^{-\gamma/\kappa}T_{1,2i}^{-1/\kappa} \tag{5}$$

It should be appreciated that equation (5) is not valid for dissolved gases, such as methane and ethane, because they relax by different processes than the longer molecules. If the diffusion or relaxation distribution was determined as function of log $D_i$ or log log $T_{1,2i}$ with the log $D_i$ or log $T_{1,2i}$ evenly spaced, then the log distribution for the proton fraction of spins on molecules with chain length $N_i$ is given by $$f_N(\log N_i) = \nu f_D(\log D_i), \tag{6}$$

$$f_N(\log N_i) = \kappa f_T(\log T_{1,2i}), \tag{7}$$

respectively. The weight fraction, on a log scale, is then given by $$w(\log N_i) = \frac{[(7N_i+1)/(N_i+1)]f_N(\log N_i)}{\int[(7N_j+1)/(N_j+1)]f_N(\log N_j)d\log(N_j)}. \tag{8}$$

In this equation, it is assumed that a molecule with $N_i$ carbon atoms has $2N_i+2$ protons. Then, on a linear scale, the weight fraction of molecules with chain length $N_i$ is given by $$w_i = w(\log N_i)/N_i \tag{9}$$

It should be appreciated that equations (2) through (5) set forth above for chain length and mean chain length as a function of diffusion coefficients and relaxation times may be derived from the observation that, for oils high in saturates, the diffusion coefficient have the form $$D_i = A\bar{N}^{-\beta}N_i^{-\nu} \tag{10}$$

and similarly for relaxation times. For small molecules such as methane and ethane, the quantity $N_i^\nu$ in Eq. (10) is modified because the molecules no longer act like chain molecules. For methane, it is replaced with 1.64, and for ethane, it is replaced with 2.73. See, Freed, D. E., et al., "Scaling laws for diffusion coefficients in mixtures of alkanes," *Phys Rev Lett.* 94:067602 (2005). In this way, the NMR relaxation and diffusion distributions can give the chain length distribution for the entire oil, not just for components below $C_6$. However, the resolution is not particularly good.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Illustrative embodiments of the present disclosure are directed to a method of analyzing a composition of a hydrocarbon-containing fluid. The method includes using a nuclear magnetic resonance (NMR) tool to conduct NMR measurements on the hydrocarbon-containing fluid to obtain NMR data. The method further includes using at least one non-NMR tool to conduct additional measurements and to obtain non-NMR data on the fluid. In some embodiments, the non-NMR tool is an optical tool, the additional measurements are optical measurements, and the non-NMR data are optical data. An indication of the composition of the fluid, such as chain length distribution, is determined by using the NMR data. The indication of the composition of the fluid is normalized using the non-NMR data.

Various embodiments of the present disclosure are also directed to a method of analyzing a composition of a hydrocarbon-containing formation fluid. The method includes locating a nuclear magnetic resonance (NMR) tool and at least one additional non-NMR tool downhole in a formation. The hydrocarbon-containing formation fluid is extracted from the formation. The NMR tool is used to conduct downhole NMR measurements and to obtain NMR data on the extracted formation fluid. The additional non-NMR tool is used to conduct additional downhole measurements and to obtain non-NMR data on the extracted formation fluid. An indication of the composition of the extracted formation fluid is determined by using the NMR data. The indication of the composition of the extracted formation fluid is normalized using the non-NMR data.

Illustrative embodiments of the present disclosure are also directed to an apparatus for analyzing a composition of a hydrocarbon-containing formation fluid. The apparatus includes a nuclear magnetic resonance (NMR) borehole tool adapted for use downhole to conduct NMR measurements downhole and to obtain NMR data on the hydrocarbon-containing formation fluid. The apparatus also includes a non-NMR borehole tool adapted for use downhole to conduct non-NMR measurements downhole and to obtain non-NMR data on the formation fluid. A processor is coupled to the NMR borehole tool and the non-NMR borehole tool. The processor determines an indication of the composition of the formation fluid using the NMR data and normalizes the indication of the composition using non-NMR data.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of embodiments of the subject disclosure, in which like reference numerals represent similar parts throughout the several views of the drawings, and wherein.

DETAILED DESCRIPTION

The particulars shown herein are by way of example and for purposes of illustrative discussion of the embodiments of the subject disclosure and are presented in the cause of providing what is believed to be the most useful and readily understood description of the principles and conceptual aspects of the subject disclosure. In this regard, no attempt is made to show structural details in more detail than is needed for the fundamental understanding of the subject disclosure, the description taken with the drawings making apparent to those skilled in the art how the several forms of the subject disclosure may be embodied in practice.

Figure 1:
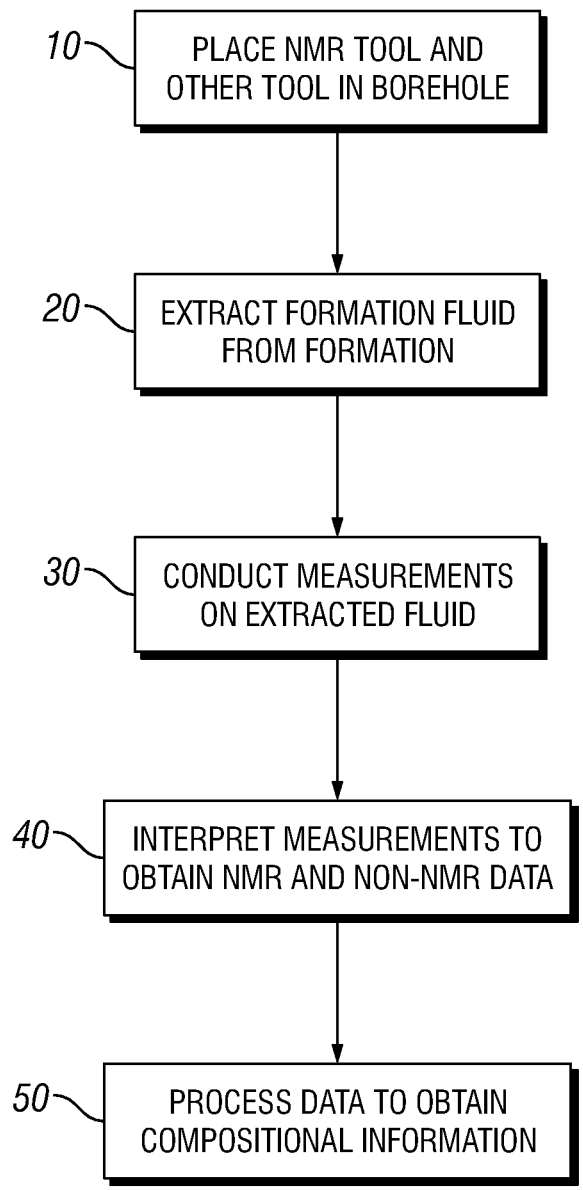
FIG. 1 is a flow chart of a disclosed method.

Turning to FIG. 1, a broad method is disclosed. At 10, one or more downhole fluid analysis logging tools used to extract fluid from a formation and to take measurements on these fluids are placed downhole. At 20, the one or more tools are used to extract fluid from a formation, and at 30, measurements (experiments) on the fluid are conducted. These measurements include NMR measurements, such as (by way of example) relaxation measurements or diffusion measurements, and at least additional non-NMR measurements such as (by way of example) optical measurements, mass density measurements, and viscosity measurements. These different measurements can be made by the same logging tool or different logging tools, but for purposes of the specification and claims even if a single tool can make both NMR and non-NMR measurements that tool will be considered as comprising multiple tools because it has multiple functions. At 40, one or more processors located downhole and/or uphole are used to interpret this raw data to obtain quantities such as (by way of example) the NMR magnetization decays, the distributions of NMR relaxation times and diffusion coefficients, optical spectra and densities, and the density and viscosity of the fluid. At 50, the processor then uses the NMR determinations and the other determinations, such as optical spectra determinations, together in order to obtain compositional information or an indication of composition, such as a chain length distribution, mean chain length, weight percent of a component, weight percent of a pseudocomponent (e.g., a combination of components), mole percent of a component, mole percent of a pseudocomponent, gas-to-oil ratio, and/or viscosity.

The NMR tool can measure, but is not restricted to a measurement of NMR diffusion, NMR longitudinal relaxation ($T_1$) NMR transverse relaxation ($T_2$), the dispersion of NMR relaxation, NMR hydrogen index, and high resolution NMR spectroscopy data. The non-NMR tool can measure, but is not restricted to a measurement of optical density, optical spectra, fluid density, viscosity, temperature, and pressure. In one aspect, as described in detail hereinafter, in addition to conducting an enhanced compositional analysis, additional information may be obtained, such as the amount of dissolved gases, such as $CO_2$, information about asphaltenes and biodegradation, and the viscosity of the oil.

In some embodiments, it is assumed that a forward model exists that allows for the prediction of the distribution of relaxation times or diffusion coefficients from the composition of the fluid. One example is the constituent viscosity model in U.S. Pat. No. 6,859,032, and another is the previously-described alkane mixture model. A third example is the empirical interpolation scheme described in Anand, V., and Freedman, R., "New methods for predicting properties of live oils from NMR," Paper AAAA *Proceedings of the 2009 Annual SPWLA Symposium* (2009). These models can be extended to treat dissolved gases such as carbon dioxide and methane.

In various embodiments, the resolution and width of the carbon chain length distribution can be enhanced by combining data from different tools. For example, the optics data is sensitive to small alkanes such as $C_1$ (methane) and $C_2$ (ethane), but it lumps the composition for hexane and larger alkanes into one pseudo-component ($C_{6+}$), such that the individual weight percents of molecules with carbon number 6 and greater are not determined. The NMR data can give the composition over the entire range of carbon numbers, but the resolution and accuracy is, in many cases, not as fine as the optics data is for the small carbon numbers such as $C_2$ through $C_5$. As described in more detail below, by using the optical data to constrain an inversion process that inverts the NMR data, or by combining the two sets of data in other manners, a chain length distribution that has greater resolution and accuracy at low carbon numbers and also covers a wider range of chain length is achieved.

In other embodiments, data from NMR is combined with data from other tools to enable a determination of the oil composition when the NMR data by itself is insufficient for obtaining chain length distributions. An example of this is when there are dissolved gases such as methane and ethane in the oil. These gases relax by different processes than the rest of the oil. See, Lo, S., et al., "Correlations of NMR relaxation time with viscosity, diffusivity, and gasoil ratio of methanehydrocarbon mixtures," *Proceedings of the 2000 Annual Technical Conference and Exhibition, Society of Petroleum Engineers* (October, 2000) and Zhang, Y. et al., "Oil and gas NMR properties: The light and heavy ends," *SPWLA 43$^{rd}$ Annual Logging Symposium*, Oslo, Japan, Paper HHH (2002) which is hereby incorporated by reference herein in its entirety. Because of this, in order to obtain chain length distributions from the relaxation data, it is useful to know the amount of methane and ethane in the oil. By combining the optics data and density data with the NMR relaxation data, it becomes possible to obtain a more robust, full chain-length distribution.

In further embodiments, data from other tools are combined with the NMR raw data to improve the inversion of the raw data and thereby improve the accuracy of the chain length distribution derived from the NMR data. In particular, obtaining NMR relaxation and diffusion distributions from the magnetization decay involves an inversion process, such as an inverse Laplace transform. There are many solutions for the distributions that are consistent with the raw data within the tolerance of the noise level. Constraining the solution for the diffusion or relaxation distributions to be consistent with oil properties, such as composition or viscosity derived from other tools, restricts the distributions to ones that better reflect these physical properties of the oil. This, in turn, provides better values for the chain length distributions. In addition, the raw data from the NMR tools can be inverted directly to chain length distributions, and, again, by constraining the distributions to agree with measurements from other tools, the accuracy of the chain length distributions can be improved.

In one embodiment, the chain length distribution from NMR is combined with the composition from an optics tool to enhance the resolution and range of the final chain length distribution. More particularly, optical data from downhole optical tools provides weight fractions for a few components below $C_6$ and lumps the additional weight fractions as $C_{6+}$. Essentially, that means that the optical tool provides no detailed information above $C_5$. Similarly but conversely, while NMR measurements provide information over a full chain length range, the resolution in the chain length distribution found by direct methods, in many cases, is quite poor between $C_1$ and $C_6$. By combining the different measurements, chain length distributions over a wide range of chain lengths can be obtained with a higher resolution than from either alone.

Information about the composition of the fluid (e.g., chain length distribution) can be normalized using the non-NMR data. The chain length distribution determined from the NMR data is normalized by rescaling the chain length distribution to make the distribution consistent with the non-NMR data. For example, suppose the weight percents $w_{c1}$, $w_{c2-c5}$ and $w_{c6+}$ have been determined from processing associated with an optical tool, and the chain length distribution $\{N_i, w_i\}$ has been determined from processing associated with an NMR tool. The optics data can be delumped according to known techniques to obtain $w_{c1}$, $w_{c2}$, $w_{c3}$, $w_{c4}$, $w_{c5}$ and $w_{c6+}$. For the new distribution, $W(N_i)$ the values of $w_{c1}$ found from the optics can be kept for carbon numbers less than 6. The $w_{c6+}$ fraction can then be used to normalize the components $w_i$ for carbon numbers $i \geq 6$ from the NMR distribution, to obtain the entire distribution. The new distribution then becomes $$W(N_i) = \begin{cases} w_{ci} & \text{for } i \leq 5 \\ w_i \dfrac{w_{c6+}}{\sum_{j \geq 6} w_j} & \text{for } i \geq 6. \end{cases} \quad (11)$$

Figure 2:
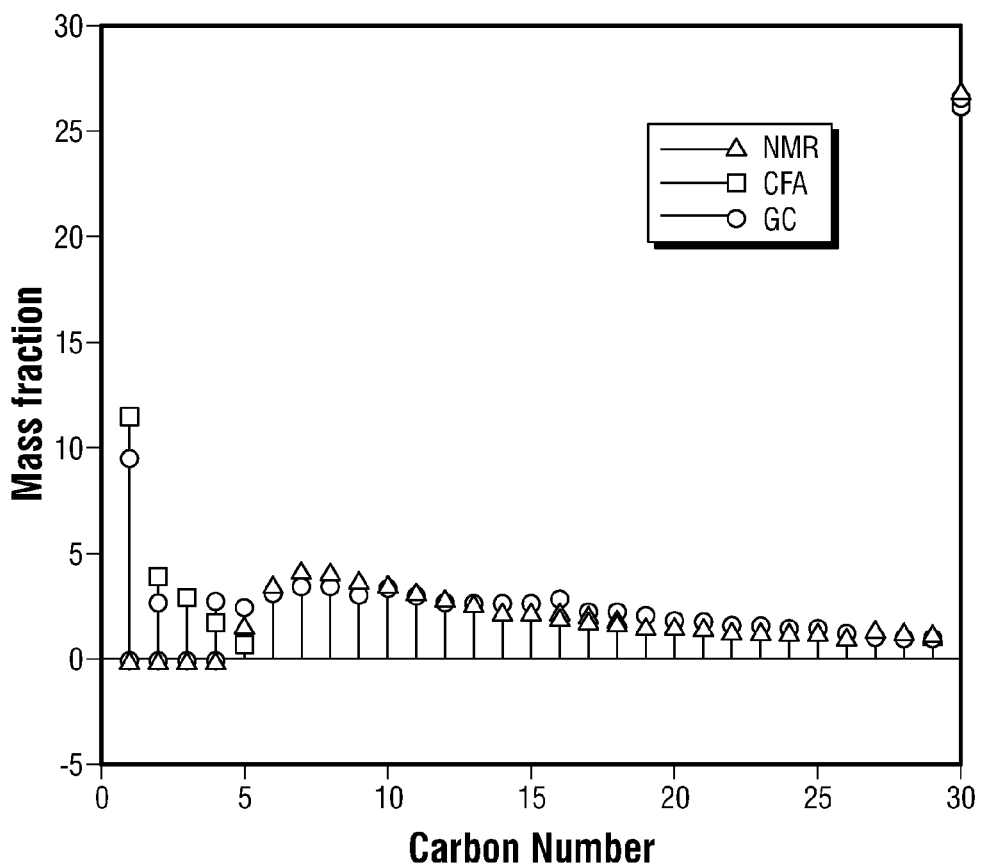
FIG. 2 are plots of the chain length distribution of an oil sample obtained from an optical tool, an NMR tool as weighted according to one embodiment, and gas chromatography.

An example is given in FIG. 2. In this case, the NMR data was taken on the dead oil (with no dissolved gases), so the NMR distribution (triangles) contains no information (i.e., the mass fraction is set to zero) for $C_1$ through $C_4$ and normalized information (based on equation (11)) for carbon chains 5 and larger. The processed (delumped) optics data on the live oil (squares) shows the weight percent up to $C_5$. The combined distribution is given by the squares for $C_1$ through $C_5$ and by the triangles for $C_6$ and above. If desired, the optics and NMR results can be averaged or weighted for $C_5$ as discussed in more detail hereinafter. The combined distribution takes into account the full range of carbon numbers measured by gas chromatography (circles) on the live oil, and as seen in FIG. 2 agrees quite well with the gas chromatography.

In some cases, the data from NMR for some of the shorter chains may also be reliable. Then this information can also be included in the final chain length distribution. For example, if the amount of methane from NMR, $w_1$, is considered to be fairly reliable, then the final chain length distribution can be taken to be $$W(N_i) = \begin{cases} aw_{c1} + (1-a)w_1 & \text{for } i \leq 5 \\ w_i \dfrac{1 - \sum_{i=1}^{5} W(N_i)}{\sum_{j \geq 6} w_j} & \text{for } i \geq 6, \end{cases} \quad (12)$$

where a is a measure of the confidence level of the optically determined $w_{c1}$ versus the NMR-determined $w_i$.

A second embodiment involves combining NMR data and data from other tools, such as optical tools, density tools, pressure tools, or viscometers, and inverting the combined data to obtain chain length distributions. The NMR data may include NMR relaxation, NMR diffusion distributions, or hydrogen index measurements. The additional data from the other tools can make it possible to obtain chain length distributions from the NMR data in cases where the inversion of the NMR data would otherwise be non-unique or the NMR data by itself is insufficient to determine the chain length distribution. It also augments the range of chain lengths that can be resolved by optics alone.

It is noted that equations (2) through (5) set forth above for the mean chain lengths and the chain lengths in terms of the diffusion or relaxation distributions also depend on pressure and temperature. Thus, to obtain the mean chain lengths and the chain length distributions from NMR measurements, it is useful to combine these measurements with pressure and temperature measurements.

It is also noted that oils often contain dissolved gases such as methane and ethane. These gases relax via different processes than the larger alkane molecules. As a consequence, they can have the same relaxation time as larger molecules, such as hexane. This makes the inversion process for the chain length distribution from relaxation distributions non-unique, unless additional information, such as the amount of methane, is known. Often, though, the relaxation measurements are taken with considerably more resolution than the diffusion measurements. This means that, in principle, they should give much higher quality chain length distributions, if the issues of the dissolved gases can be resolved, and if there is little to no asphaltene in the oil. In some cases, diffusion measurements are not made. Thus, it is useful to have a method for calculating the chain length distribution from relaxation times.

It is also noted that dissolved carbon dioxide ($CO_2$) changes the density and free volume of the oil, and thus influences the diffusion coefficients and relaxation times of the oil. However, the $CO_2$ is not directly observed by downhole NMR tools. As a result, if there is a substantial amount of $CO_2$ in the oil, just applying equations (2) through (5) will not give an accurate chain length distribution. To properly account for the effects of $CO_2$, it is useful to have an independent measure of $CO_2$.

With respect to the second embodiment what follows is a detailed example for determining the chain length distribution from the relaxation time distribution when there is a substantial amount of methane in the oil. Other hydrocarbon gases such as ethane can be treated similarly. For dissolved methane, spin rotation and intermolecular relaxation are the dominant contribution to its relaxation. This is in contrast to most other alkanes, where intramolecular relaxation is the dominant mode of relaxation. A model for these effects can be found in Lo, S., et al., "Correlations of NMR relaxation time with viscosity, diffusivity, and gasoil ratio of methane-hydrocarbon mixtures," *Proceedings of the* 2000 *Annual Technical Conference and Exhibition, Society of Petroleum Engineers* (October, 2000), but other models can be used instead. In the aforementioned Lo, S., et al., reference, the intermolecular relaxation rate $T_1$ of methane is given by $$\left(\frac{1}{T_1}\right)_{inter} = \frac{32\pi^2\gamma^4\hbar^2 I(I+1)N\rho_n\eta}{15kT}, \quad (13)$$

where $\gamma$ is the gyromagnetic ratio, h is Planck's constant, $I=\frac{1}{2}$ is the spin of the proton, N is the number of spins per molecule, $\rho_n$ is the number density of molecules, k is Boltzmann's constant, T is temperature, and $\eta$ is the viscosity of the oil. The viscosity of the oil can be determined by a viscometer or calculated from the NMR diffusion or relaxation distribution. The product $N\rho_n$ is the number of spins per unit volume, which is equal to the hydrogen index HI. This can be measured directly by NMR tools.

The relaxation rate due to spin rotation is $$\left(\frac{1}{T_1}\right)_{SR} = \frac{c_1\rho}{T^{c_2}}, \quad (14)$$

where, in the aforementioned Lo, S., et al. reference, $c_1=1.57*10^5$, $c_2=1.50$ and $\rho$ is the density in g/m³. The total relaxation of methane $T_{1,2\,meth}$ is then given by $$T_{1,2meth} = \left[\left(\frac{1}{T_1}\right)_{inter} + \left(\frac{1}{T_1}\right)_{SR}\right]^{-1}. \quad (15)$$

This depends on density, hydrogen index, viscosity and temperature. The hydrogen index can be measured with NMR tools. The density can be measured with a densimeter or can be calculated from pressure measurements, and the viscosity can be measured by a viscometer or calculated from NMR diffusion or relaxation measurements. The downhole temperature is also measured by logging tools.

According to equation (5), the other components of the oil (assuming no other dissolved gases and no asphaltene) have a $T_1$ and $T_2$ given by $$T_{1,2i} = B\overline{N}^{-\gamma}N_i^{-\kappa} \quad (16)$$

The composition can be found by finding $\overline{N}$. One possibility is to use the value of $\overline{N}$ from diffusion measurments. In some wireline tools, the diffusion is not measured with sufficient resolution to obtain a full chain length distribution, but it can still be used to obtain the mean chain length. It is also possible to solve for the mean chain length directly from the relaxation data by starting with the $1/\kappa^{th}$ moment of $T_1$ or $T_2$, which can be expressed in terms of the relaxation distribution as $$\langle T^{1/\kappa}\rangle = \frac{\int f_T(\log T_{1,2})T_{1,2}^{1/\kappa} d\log(T_{1,2})}{\int f_T(\log T_{1,2}) d\log(T_{1,2})}. \quad (17)$$

In terms of the chain length distribution, this is equivalent to $$\langle T^{1/\kappa}\rangle = \Sigma p_i T_{1,2}^{1/\kappa}(N_i), \quad (18)$$

where $p_i$ is the proton fraction, given by $$p_i = \frac{(2N_i+2)x_i}{\sum(2N_j+2)x_j} = \frac{(N_i+1)x_i}{\overline{N}+1}. \quad (19)$$

In this example, it is assumed that for the components in the oil with i>1, the relaxation time $T_{1,2}(N_i)$ is given by equation (16), while for i=1 it is equal to $T_{1,2meth}$. Substituting this into equation (18) for the $1/\kappa^{th}$ moment of the relaxation time, and rearranging the terms results in $$\langle T^{1/\kappa}\rangle = \sum_{i\geq 1}\frac{p_i}{N_i}B^{1/\kappa}\overline{N}^{-\gamma/\kappa} - \frac{p_1}{N_1}B^{1/\kappa}\overline{N}^{-\gamma/\kappa} + p_1 T_{1,2meth}^{1/\kappa}. \quad (20)$$

Next, equation (19) can be used for $p_i$, to express it in terms of the mole fraction, $x_i$, thus obtaining $$\langle T^{1/\kappa} \rangle = \frac{\sum_{i\geq 1}(N_i+1)x_i/N_i}{\overline{N}+1}B^{1/\kappa}\overline{N}^{-\gamma/\kappa} - \frac{2x_1}{\overline{N}+1}B^{1/\kappa}\overline{N}^{-\gamma/\kappa} + \frac{2x_1}{\overline{N}+1}T_{1,2meth}^{1/\kappa}. \quad (21)$$

The right-hand side of this equation contains the sum $\sum_{i\geq 1}(N_i+1)x_i/N_i = 1 + \sum_{i\geq 1}x_i/N_i$. The latter sum is considerably less than one unless there is a lareg quanitity of dissolved gas in the oil. In the case, where the only dissolved gas is methane, it can be approximated by its first term, $x_1$ resulting in $$(\overline{N}+1)\langle T^{1/\kappa} \rangle = B^{1/\kappa}\overline{N}^{-\gamma/\kappa}(1-x_1) + 2x_1 T_{1,2meth}^{1/\kappa} \quad (22)$$

If the weight percent of methane $w_{c1}$ which can be measured by the optical tools is known, $x_1$ can be expressed in terms of $w_{c1}$ using the equation $$w_{c1} = \frac{14N_1+2}{\sum_j 14N_j+2}x_1 = \frac{8}{7\overline{N}+1}x_1. \quad (23)$$

This can be substituted into equation (22) to remove $x_1$. In the resulting equation, the unknown is $\overline{N}$, which can be solved for numerically. Once a solution is obtained for $\overline{N}$, then equation (16) gives the relation between $N_i$ and $T_{1,2i}$ for $i>1$. Equations (7), (8) and (9) can then be used to find the chain length distribution, with one modification. The weight percent of methane is given by $w_{c1}$. However, the NMR methane signal occurs at $T_{1,2meth}$, and before $f(\log T_{1/2i})$ is substituted into equation (7), this extra signal should be subtracted off. Thus, Eq. (7) is replaced by $$f_N(\log N_i) = \kappa[f_T(\log T_{1,2i}) - M_0 p_1 g(\log(T_{1,2meth}) - \log(T_{1,2i}))]. \quad (24)$$

where the function g is an approximate delta-function that is peaked at $T_{1,2meth} = T_{1,2i}$ and has an area of one. The magnetization $M_0$ can be found from the initial magnetization in a $T_2$ decay. It is also the area under the $T_2$ distribution. Alternatively, it is the zero'th moment of the $T_2$ decay and can be calculated using the Mellin transform. Similarly, $\langle T_2^{1/\kappa} \rangle$ can be calculated from the $T_2$ distribution or directly from the magnetization decay. See, Venkataramanan L., et al., "Mellin transform of CPMG data," *J. Magn. Reson.*, 206:20-31 (2010) which is hereby incorporated by reference herein in its entirety.

In other embodiments, the raw data from NMR can be combined with data from one or more of optics, density, viscosity and pressure downhole measurement tools to improve the inversion process for the physical properties from the NMR data. One example of this is using results from tools, such as optics or the viscometer, to constrain the inversions for $T_1$, $T_2$ or diffusion to obtain distributions that are consistent with this other data. More particularly, NMR distributions are obtained using an inverse Laplace transform of the magnetization decay. However, this inverse Laplace transform is ill-conditioned, which means that when the signal has noise, there are many solutions which fit the data. In many cases some constraint, such as smoothness of the distribution, is imposed to restrict the solution to more physical ones.

Once a property of the oil is known, such as its viscosity, $\eta$, or the weight percent of methane, $w_{c1}$, this property can be expressed as a function of the $f_j$ and the diffusion coefficients $D_j$ or the relaxation times $T_{1,2j}$. Then these known values can be used as constraints for a minimization as previously described (e.g., the quantity $\|d-Kf\|^2$ is minimized using methods such as a non-negative least square fit with Tikhonov regularization or by maximum entropy methods). To illustrate this, consider the example where the viscosity $\eta_{meas}$ has been measured by some other method. Then, it is possible to solve for a diffusion distribution for the NMR data that also has a viscosity equal to $\eta_{meas}$. This can be done by obtaining a diffusion coefficient from the NMR data, calculating the viscosity $\eta(\{f_j,D_j\})$ for this distribution and comparing this calculated viscosity with the measured viscosity. If the calculated viscosity is very different from the measured one, the NMR inversion is redone to obtain another distribution iteratively until the calculated viscosity is consistent with the measured data. Mathematically, this could be done by a joint inversion by minimizing $\|k-Kf\|^2$ while satisfying the condition that $\|\eta_{meas}-\eta(\{f_j,D_j\})\|$ is less than the experimental tolerance. Most optimization packages can honor this condition along with the usual positivity contraint that $f_j\geq 0$.

It is also possible to constrain the viscosity $\eta(\{f_j,D_j\})$ found from the diffusion distribution according to equation (1) to equal the measured quantity by minimizing the expression $$\|d-Kf\|^2 + \lambda\|\eta_{meas}-\eta(\{f_j,D_j\})\|^2 \quad (25)$$

where $\lambda$ is a parameter that reflects how strong the constraint is. Constraining the calculated viscosity to equal the measured viscosity can help improve the inversion process for the diffusion distribution. Once this distribution has been found, it can be used to solve for the chain length distribution, as described above. It should be appreciated that this method will also apply to relaxation distributions and other physical properties that can be expressed in terms of the diffusion distributions or relaxation distributions.

In other embodiments, the raw data from a downhole NMR tool is combined with data from other downhole tools to invert directly for information about the composition. For example, in the case of diffusion, variables can be chosen as $\{N_j,f(N_j)\}$ instead of $\{D_j,f_j\}$. The $N_j$ can be linearly spaced, for example $N_j=j$ for $j=1, 2, 3, \ldots$, or another spacing can be chosen. Then the kernel can be defined in terms of these new variables as $$K_{ij}(\{N_j\}) = \exp(-b_i D(N_j)) \quad (26)$$

where $D(N_j)$ is given by equation (10), with the appropriate modification for methane and ethane. This equation depends on the mean chain length, which, in turn, depends on the entire distribution. A non-linear minimization can be conducted, where the kernel changes with the fit, or $\overline{N}$ can be determined directly from the raw data, using methods in previously incorporated Venkataramanan L., et al., "Mellin transform of CPMG data", *J. Magn. Reson.*, 206:20-31 (2010). In the latter case, for a given measurement, the kernel is fixed, and the minimization can be linear, apart from the usual non-negativity constraint. In particular, consider the example where the methane weight percent $w_{c1}$ is known from optical measurements. The proton number for methane, $f(N_1)$, can be expressed in terms of $w_{c1}$ as follows:

$$f(N_1) = M_0 \frac{N_1+1}{7N_1+1} \frac{7\overline{N}+1}{\overline{N}+1} w_{c1}, \quad (27)$$

where, as in the example above, $M_0$ and $\overline{N}$ come from moments of the magnetization decay and can be calculated directly from the raw data. In this equation, it is again assumed that a molecule with carbon number $N_i$ has $2N_i+2$ protons. Depending on the oil, other assumptions can be made instead. To obtain this equation, use has been made of the relation between the proton number $f(N_i)$ and the mole fraction $x_i$ given by $$f(N_i) = \frac{(2N_i + 2)x_i}{\sum_j (2N_j + 2)x_j} M_0 = \frac{(2N_i + 2)x_i}{2\overline{N} + 2} M_0, \quad (28)$$

and the relation between the weight percent and the proton number $$w_{ci} = \frac{(14N_i + 2)x_i}{\sum_j (14N_j + 2)x_j} = \frac{(14N_i + 2)x_i}{14\overline{N} + 2}. \quad (29)$$

Thus, equation (27) can be used to fix the value of $f(N_1)$ to the value determined by $w_{c1}$, $\overline{N}$, and $M_0$. Then the expression $\|d-K(\{N_j\})f\|^2$ can be minimized to solve for $f(N_i)$ with $i \geq 2$, while holding $f(N_1)$ fixed. This minimization can be done using standard non-negative least squares techniques and regularization schemes such as Tikhonov regularization. Alternatively, maximum entropy methods can be used.

Optical data can also be combined with NMR relaxation measurements to determine fluid composition. For example, a log-linear scaling law can be used to relate component T2 relaxation time to component chain length. The scaling law can be used to obtain fluid mixture component weight fractions from the NMR relaxation measurements. Moreover, optical data can be used with the NMR measurements and the scaling law to obtain further refined estimates for these component weight fractions. U.S. patent application Ser. No. 14/109,354 filed on Dec. 17, 2013 and referenced above describes this method in further detail and is hereby incorporated by reference in its entirety.

According to one aspect, these methods are not limited to a single component in the distribution but, instead, can apply to any combination of components. In addition, if a component such as $w_{c1}$ is known with some level of uncertainty, and the NMR on its own also can give $f(N_1)$ with some level of uncertainty, instead a constraint can be introduced as in the previous example. This can be done by implementing a joint inversion which minimizes the expression $$\|d-K(\{N_j\})f\|^2 \quad (30)$$

while satisfying the condition that $$\|w_1-w_{c1}\| < \text{the experimental tolerance} \quad (31)$$

where $w_{c1}$ is the measured quantity and $w_1$ is calculated from $f(N_j)$ according to equation (27). Alternatively, a regularization technique can be used, such as minimizing the expression $$\|d-K(\{N_j\})f\|^2 + \lambda\|w_1-w_{c1}\|^2 \quad (32)$$

over the $f(\{N_j\})$. The $f(N_i)$ are also constrained to be positive. In the above expression, $\lambda$ depends on the uncertainty of the two measurements, and $w_1$ can be obtained from $f(N_j)$ using equation (27). In this way, by combining information from other tools, the inversion for chain length from NMR can be improved.

Similar methods can also be used if pseudo-components are determined from the optics. For example, when the weight percent $w_{c3-c5}$ of the pseudo-component $C_{3-5}$ is measured, this is the sum of the individual weight percents $w_3$, $w_4$ and $w_5$ of $C_3$, $C_4$ and $C_5$. In this case, $w_3$, $w_4$ and $w_5$ can be determined directly from the $f(N_i)$ with the help of equations (28) and (29). Then the expression $\|d-K(\{N_j\})f\|^2$ can be minimized with the constraint that $w_3+w_4+w_5=w_{c3-c5}$. The methods described above can also be used to obtain the chain length distribution from relaxation time distributions, if the weight percent of methane and the density of the oil are known.

In another embodiment, the NMR data can be used to improve fluid composition determinations made from the optics data. In particular, if there is a small amount of water (under about 5%), and the water and hydrocarbon volumes can be determined from the NMR data, then these values can be used to constrain the estimation of fluid composition from the optics data. In one method, different models for two-phase flow can be applied to the optics data, and the ones that give the accurate water and hydrocarbon fractions can then be used in determining the hydrocarbon composition from the optics data. The volume fraction of water can also be used to constrain the optics data to determine the amount of carbon dioxide in the sample. This information can then be used to improve the determination of the composition of the oil or gas in the sample from the NMR data.

According to one aspect, the previously-described methods can be used to analyze the composition of a hydrocarbon-containing fluid not only downhole, but in a laboratory or uphole at a wellsite. By way of example, a hydrocarbon-containing fluid is subject to an NMR relaxation or diffusion experiment in order to obtain NMR relaxation or diffusion data as well as to a non-NMR experiment such as an optical experiment to obtain non-NMR data such as optical data. The data obtained by the non-NMR experiment is then used to modify the analysis of the NMR data in determining indications of the composition. By way of example, optical data may be used to constrain an inversion of the NMR data.

According to a further aspect, the previously-described methods can be used in conjunction with single-phase samples (e.g., liquid), and multi-phase samples (e.g., liquid and gas) including emulsions. The previously-described methods can also be used in conjunction with samples containing water.

Figure 3:
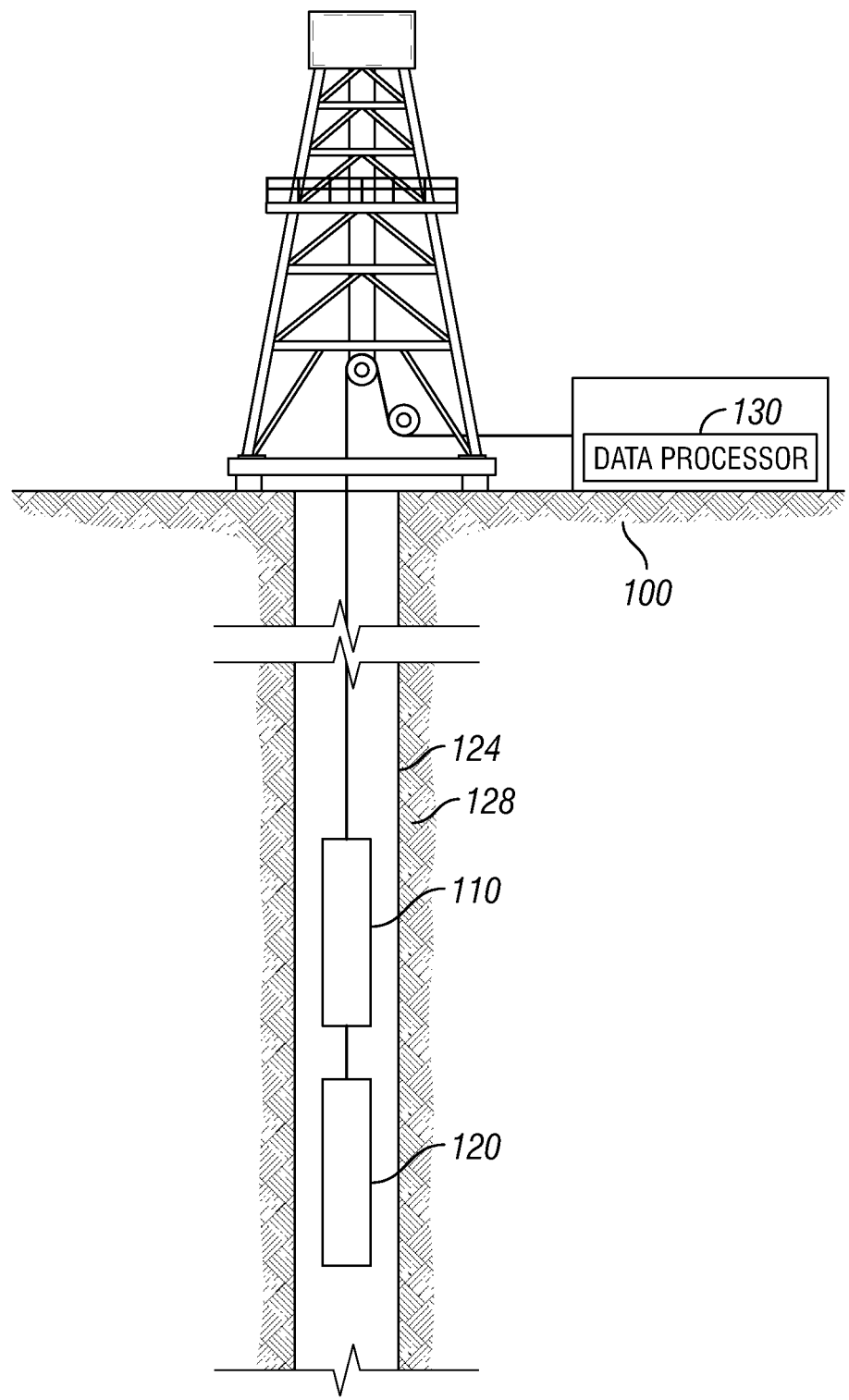
FIG. 3 is an apparatus for implementing disclosed methods.

According to another aspect, as seen in FIG. 3, an apparatus 100 is provided for implementing the previously-described methods. The apparatus 100 includes a tool string including an NMR borehole tool 110 and a non-NMR borehole tool 120, shown located in a borehole 124 of a formation 128, and a processor 130 that is coupled to tools 110 and 120. The NMR borehole tool 110 may be any commercially available NMR tool or any proposed tool capable of conducted NMR measurements downhole. In one embodiment, the NMR borehole tool 110 is capable of conducting NMR relaxation and/or diffusion measurements on a hydrocarbon-containing fluid sample. The non-NMR tool 120 may be any commercially available non-NMR tool or any proposed tool of conducted non-NMR measurements downhole that are useful in modifying an NMR data analysis, e.g., by being useful in constraining an inversion of the NMR data. In one embodiment, the non-NMR tool 120 is a formation tester instrument such as the CFA™ tool that is capable of optically scanning the hydrocarbon-containing fluid sample that is located in a flowline of the tool. The processor 130, although shown on the surface of formation 128, may be part of either or both of tools 110 and 120 or may be a separate processor that may be located downhole or uphole. The processor may be a programmed computer, a dedicated processor, a microprocessor, a system of microprocessors, a digital signal processor (DSP), an application-specific integrated circuit (ASIC), or other circuitry capable of analyzing the NMR data obtained by tool 110 in light of the data obtained by tool 120.

Although only a few example embodiments have been described in detail above, those skilled in the art will readily appreciate that many modifications are possible in the example embodiments without materially departing from this disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method of analyzing a composition of a hydrocarbon-containing fluid, the method comprising:
   (a) using a nuclear magnetic resonance (NMR) tool to conduct NMR measurements on the hydrocarbon-containing fluid to obtain NMR data;
   (b) using at least one non-NMR tool to conduct additional measurements and to obtain non-NMR data on the fluid; and
   (c) determining an indication of the composition of the fluid by using the NMR data; and
   (d) normalizing the indication of the composition of the fluid using the non-NMR data.

2. A method according to claim 1, wherein the indication of the composition comprises a chain length distribution.

3. A method according to claim 1, wherein the NMR measurements comprise at least one of relaxation measurements and diffusion measurements.

4. A method according to claim 3, wherein the NMR data comprise at least one of NMR magnetization decays, distributions of NMR relaxation times, and distributions of NMR diffusion coefficients.

5. A method according to claim 1, wherein the non-NMR tool is an optical tool, the additional measurements are optical measurements, and the non-NMR data are optical data.

6. A method according to claim 5, wherein the optical data comprise at least one of optical spectra and optical densities.

7. A method according to claim 5, wherein the indication of the composition comprises a chain length distribution and the optical data is used to normalize the chain length distribution according to:

$$W(N_i) = \begin{cases} w_{ci} & \text{for } i \leq 5 \\ w_i \dfrac{w_{c6+}}{\sum_{j \geq 6} w_j} & \text{for } i \geq 6 \end{cases}.$$

where $W(N_i)$ is the chain length distribution, i is an index of the number of carbon atoms in a particular component of the composition, $w_i$ is the weight fraction of molecules with chain length $N_i$ as determined by the NMR measurements, $w_{c1}$ is a weight percentage for the carbon molecule with index i, and $w_{c6+}$ is a weight percentage determined according to the optical data of components having a chain of at least six carbon molecules.

8. A method according to claim 5, wherein the indication of the composition comprises a chain length distribution and the optical data is used to normalize the chain length distribution according to:

$$W(N_i) = \begin{cases} aw_{c1} + (1-a)w_1 & \text{for } i \leq 5 \\ w_i \dfrac{1 - \sum_{i=1}^{5} W(N_i)}{\sum_{j \geq 6} w_j} & \text{for } i \geq 6 \end{cases},$$

where $W(N_i)$ is the chain length distribution, i is an index of the number of carbon atoms in a particular component of the composition, $w_i$ is the weight fraction of molecules with chain length $N_i$ as determined by the NMR measurements, $w_{ci}$ is a weight percentage for the carbon molecule with index i, $w_{c6+}$ is a weight percentage determined according to the optical data of components having a chain of at least six carbon molecules, and a is measure of confidence level.

9. A method of analyzing a composition of a hydrocarbon-containing formation fluid, the method comprising:
   (a) locating a nuclear magnetic resonance (NMR) tool and at least one additional non-NMR tool downhole in a formation;
   (b) extracting the hydrocarbon-containing formation fluid from the formation;
   (c) using the NMR tool to conduct downhole NMR measurements and obtain NMR data on the extracted formation fluid and using the at least one additional non-NMR tool to conduct additional downhole measurements and obtain non-NMR data on the extracted formation fluid;
   (d) determining an indication of the composition of the extracted formation fluid by using the NMR data; and
   (e) normalizing the indication of the composition of the extracted formation fluid using the non-NMR data.

10. A method according to claim 9, wherein the indication of the composition comprises a chain length distribution.

11. A method according to claim 9, wherein the NMR measurements comprise at least one of relaxation measurements and diffusion measurements.

12. A method according to claim 11, wherein the NMR data comprise at least one of NMR magnetization decays, distributions of NMR relaxation times, and distributions of NMR diffusion coefficients.

13. A method according to claim 9, wherein the non-NMR tool is an optical tool, the additional measurements are optical measurements, and the non-NMR data are optical data.

14. A method according to claim 13, wherein the optical data comprise at least one of optical spectra and optical densities.

15. A method according to claim 13, wherein the indication of the composition comprises a chain length distribution and the optical data is used to normalize the chain length distribution according to:

$$W(N_i) = \begin{cases} w_{ci} & \text{for } i \leq 5 \\ w_i \dfrac{w_{c6+}}{\sum_{j \geq 6} w_j} & \text{for } i \geq 6 \end{cases}.$$

where $W(N_i)$ is the chain length distribution, i is an index of the number of carbon atoms in a particular component of the composition, $w_i$ is the weight fraction of molecules with chain length $N_i$ as determined by the NMR measurements, $w_{ci}$ is a weight percentage for the carbon molecule with index i, and $w_{c6+}$ is a weight percentage determined according to the optical data of components having a chain of at least six carbon molecules.

16. A method according to claim 13, wherein the indication of the composition comprises a chain length distribution and the optical data is used to normalize the chain length distribution according to:

$$W(N_i) = \begin{cases} aw_{c1} + (1-a)w_1 & \text{for } i \leq 5 \\ w_i \dfrac{1 - \sum_{i=1}^{5} W(N_i)}{\sum_{j \geq 6} w_j} & \text{for } i \geq 6 \end{cases},$$

where $W(N_i)$ is the chain length distribution, i is an index of the number of carbon atoms in a particular component of the composition, $w_i$ is the weight fraction of molecules with chain length $N_i$ as determined by the NMR measurements, $w_{ci}$ is a weight percentage for the carbon molecule with index i, $w_{c6+}$ is a weight percentage determined according to the optical data of components having a chain of at least six carbon molecules, and a is measure of confidence level.

17. An apparatus for analyzing a composition of a hydrocarbon-containing formation fluid, the apparatus comprising:

a nuclear magnetic resonance (NMR) borehole tool adapted for use downhole to conduct NMR measurements downhole and obtain NMR data on the hydrocarbon-containing formation fluid;
a non-NMR borehole tool adapted for use downhole to conduct non-NMR measurements downhole and obtain non-NMR data on the formation fluid;
a processor coupled to the NMR borehole tool and the non-NMR borehole tool, wherein the processor is configured to (i) determine an indication of the composition of the formation fluid using the NMR data and (ii) normalize the indication of the composition using non-NMR data.

18. An apparatus according to claim 17, wherein the non-NMR borehole tool is an optical tool and the non-NMR data is optical data.

19. An apparatus according to claim 17, wherein the indication of the composition comprises a chain length distribution.

20. An apparatus according to claim 18, wherein the indication of the composition comprises a chain length distribution and the optical data is used to normalize the chain length distribution according to:

$$W(N_i) = \begin{cases} w_{ci} & \text{for } i \leq 5 \\ w_i \dfrac{w_{c6+}}{\sum_{j \geq 6} w_j} & \text{for } i \geq 6 \end{cases}.$$

where $W(N)$ is the chain length distribution, i is an index of the number of carbon atoms in a particular component of the composition, $w_i$ is the weight fraction of molecules with chain length $N_i$ as determined by the NMR measurements, $w_{ci}$ is a weight percentage for the carbon molecule with index i, and $w_{c6+}$ is a weight percentage determined according to the optical data of components having a chain of at least six carbon molecules.

* * * * *